United States Patent [19]
Zoller et al.

[11] Patent Number: 5,554,594
[45] Date of Patent: Sep. 10, 1996

[54] IMIDAZOLIDINE DERIVATIVES

[75] Inventors: Gerhard Zoller, Schöneck; Bernd Jablonka, Bad Soden; Melitta Just, Langen; Otmar Klingler, Rodgau; Gerhard Breipohl, Frankfurt am Main; Jochen Knolle, Kriftel; Wolfgang König, Stallwang, all of Germany

[73] Assignee: Cassella Aktiengesellschaft, Frankfurt am Main, Germany

[21] Appl. No.: 456,066

[22] Filed: May 31, 1995

Related U.S. Application Data

[63] Continuation of Ser. No. 98,123, Jul. 27, 1993, abandoned.

[30] Foreign Application Priority Data

Aug. 28, 1992 [DE] Germany ............ 42 28 717.0

[51] Int. Cl.$^6$ .................... C07D 233/76; A61K 37/02
[52] U.S. Cl. .................. 514/18; 514/19; 514/20; 548/319.5; 548/350.1; 548/352.1; 548/354.1
[58] Field of Search ............ 548/319.5, 350.1, 548/352.1, 354.1; 514/18, 19, 20

[56] References Cited

U.S. PATENT DOCUMENTS 5,389,614   2/1995   Konig et al. .................. 514/18

FOREIGN PATENT DOCUMENTS 73643   10/1991   Australia .

*Primary Examiner*—Richard L. Raymond
*Assistant Examiner*—Brian G. Bembenick
*Attorney, Agent, or Firm*—Perman & Green

[57] ABSTRACT

The present invention relates to compounds of the general formula I

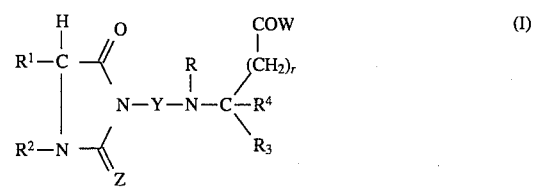

in which R, R$^1$ to R$^4$, r, Y, Z and W are defined as indicated in the description, a process for their preparation and their use as inhibitors of platelet aggregation, metastasis of carcinoma cells and osteoclast binding to the bone surfaces.

18 Claims, No Drawings

IMIDAZOLIDINE DERIVATIVES

This is a continuation of application Ser. No. 08/098,123 filed on Jul. 27, 1993 (abandoned).

The present invention relates to imidazolidine derivatives, their preparation and their use as inhibitors of blood platelet aggregation.

Hydantoin derivatives having platelet aggregation-inhibiting action are described in EP-A 449,079. Further research has shown that the compounds of the present invention are also potent inhibitors of blood platelet aggregation.

The present invention relates to compounds of the general formula I $$
\begin{array}{c}
\text{H} \quad \text{O} \quad \quad \text{COW} \\
R^1-\text{C} \underset{R^2-N}{\overset{}{\diagup}} \hspace{-2pt} \underset{\text{Z}}{\overset{}{\diagdown}} \hspace{-8pt} \begin{array}{c} R \quad (CH_2)_r \\ | \\ N-Y-N-C-R^4 \\ \quad \quad R_3 \end{array}
\end{array} \quad (I)
$$

in which

Y denotes $-(CH_2)_m-CO-$, where m represents an integer from to 4, or r denotes a number from 0 to 3;

Z denotes oxygen or sulphur;

W denotes a) hydroxyl or b) $(C_1-C_{28})$-alkoxy, $(C_6-C_{14})$-aryl-$(C_1-C_8)$-alkoxy, $(C_6-C_{14})$-aryloxy, amino or mono- or di-$(C_1-C_{18})$-alkylamino;

R denotes hydrogen or $(C_1-C_6)$-alkyl;

$R^1$ denotes $-(CH_2)_n-NH-X$, where n represents an integer from 1 to 6, $-(CH_2)_p-C_6H_4-NH-X$ or $-(CH_2)_p-C_6H_4-(CH_2)_q-C(=NX^2)-NH_2$, where p represents an integer from 1 to 3 and q represents a number from 0 to 2, but also where instead of $$\diagdown\!\!\!\!\!\!/\text{CH}-R^1 \qquad \diagdown\!\!\!\!\!\!/ \text{C}=\text{CH}-C_6H_4-X^1$$

can be present;

X, if W has one of the meanings mentioned under b) or W represents hydroxyl and q represents 2 and r is not equal to 1, denotes hydrogen, $(C_1-C_6)$-alkyl, $(C_1-C_6)$-alkoxycarbonyl, $(C_1-C_6)$-alkylcarbonyl, $(C_1-C_{18})$-alkylcarbonyloxy-$(C_1-C_6)$-alkoxycarbonyl, $(C_6-C_{14})$-aryloxycarbonyl, $(C_6-C_{14})$-aryl-$(C_1-C_6)$-alkoxycarbonyl, cyano, hydroxyl, $(C_1-C_6)$-alkoxy, amino or a radical of the formula II $$R'-NH-C=N-R'' \qquad (II)$$

in which R' and R" independently of one another represent hydrogen, $(C_1-C_6)$-alkyl, $(C_1-C_6)$-alkoxycarbonyl, $(C_1-C_6)$-alkylcarbonyl, $(C_1-C_{18})$-alkylcarbonyloxy-$(C_1-C_6)$-alkoxycarbonyl, $(C_6-C_{14})$-aryloxycarbonyl, $(C_6-C_{14}l)$-aryl-$(C_1-C_6)$-alkoxycarbonyl, cyano, hydroxyl, $(C_1-C_6)$-alkoxy or amino and if W represents hydroxyl, r is equal to 1 and q denotes 0 or 1, has one of the abovementioned meanings, with the exception of hydrogen and $(C_1-C_6)$-alkyl, it moreover not being possible for R' and R" to both represent hydrogen and/or $(C_1-C_6)$-alkyl;

$X^1$ denotes $-(CH_2)_q-NH-X$ or $-(CH_2)_q-C(=NX^2)-NH_2$;

$X^2$, if W has one of the meanings mentioned under b) or W represents hydroxyl and q represents 2 and r is unequal to 1, denotes hydrogen, $(C_1-C_6)$-alkyl, $(C_1-C_6)$-alkoxycarbonyl, $(C_1-C_6)$-alkylcarbonyl, $(C_1-C_{18})$-alkylcarbonyloxy-$(C_1-C_6)$-alkoxycarbonyl, $(C_6-C_{14})$-aryloxycarbonyl, $(C_6-C_{14})$-aryl-$(C_1-C_6)$-alkoxycarbonyl, cyano, hydroxyl, $(C_1-C_6)$-alkoxy or amino and if W represents hydroxyl, r is equal to 1 and q denotes 0 or 1, has one of the abovementioned meanings, with the exception of hydrogen;

$R^2$ denotes hydrogen or $(C_1-C_6)$-alkyl;

$R^3$ denotes hydrogen or phenyl;

$R^4$ denotes hydrogen, $-COOR^5$, $-CO-N(CH_3)-R^5$ or $-CO-NH-R^5$;

$R^5$ denotes hydrogen or $(C_1-C_{28})$-alkyl, which is optionally monosubstituted or polysubstituted by identical or different radicals from the series consisting of hydroxyl, hydroxycarbonyl, aminocarbonyl, mono- or di-$(C_1-C_{18})$-alkylaminocarbonyl, amino-$(C_2-C_{14})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2-C_{14})$-alkylaminocarbonyl, phenyl-$(C_1-C_8)$-alkoxycarbonyl, amino, mercapto, $(C_1-C_{18})$-alkoxy, $(C_1-C_{18})$-alkoxycarbonyl, $(C_3-C_8)$-cycloalkyl, halogen, nitro, trifluoromethyl or a radical $R^6$;

$R^6$ denotes $(C_6-C_{14})$-aryl, $(C_6-C_{14})$-aryl-$(C_1-C_8)$-alkyl, a monocyclic or bicyclic 5- to 12-membered heterocyclic ring which can be aromatic, partially hydrogenated or completely hydrogenated and which, as the heteroelement, can contain one, two or three identical or different nitrogen, oxygen or sulphur atoms, or denotes a radical $R^7$ where the aryl radical and, independently thereof, the heterocyclic radical can be optionally monosubstituted or polysubstituted by identical or different radicals from the series consisting of $(C_1-C_{18})$-alkyl, $(C_1-C_{18})$-alkoxy, halogen, nitro and trifluoromethyl;

$R^7$ denotes $-NR^8R^9$, $-OR^8$, $-SR^8$, an amino acid side chain, a natural or unnatural amino acid residue, imino acid residue, optionally $N-(C_1-C_8)$-alkylated or $(C_6-C_{14})$-aryl-$(C_1-C_8)$-alkylated azaamino acid residue or dipeptide residue, in which the peptide bond can be reduced to $NH-CH_2$, and also their esters and amides, where free functional groups can optionally be substituted by hydrogen or hydroxymethyl or protected by protective groups customary in peptide chemistry, or denotes a radical $-COR^{7'}$, in which $R^{7'}$ is defined as $R^7$;

$R^8$ denotes hydrogen, $(C_2-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$arylcarbonyl, $(C_6-C_{14})$-aryl-$(C_1-C_8)$-alkylcarbonyl, or $(C_6-C_{14})$-aryl-$(C_1-C_{18})$-alkoxycarbonyl, where the alkyl groups can optionally be substituted by an amino group, a natural or unnatural amino acid residue, imino acid residue, optionally $N-(C_1-C_8)$-alkylated or $(C_6-C_{14})$-aryl-$(C_1-C_8)$-alkylated azaamino acid residue or a dipeptide residue, in which the peptide bond can be reduced to $NH-CH_2$; and $R^9$ denotes hydrogen, $(C_1-C_{18})$-alkyl, $(C_6-C_{14})$-aryl or $(C_6-C_{14})$-aryl-$(C_1-C_8)$-alkyl;

and their physiologically tolerable salts.

Alkyl radicals can be straight-chain or branched. Preferred alkyl radicals are methyl, ethyl, n-propyl, i-propyl, n-butyl, i-butyl, sec-butyl and tert-butyl. The same applies to radicals such as alkoxy, alkoxycarbonyl or aralkyl.

$(C_3-C_8)$-Cycloalkyl radicals are in particular cyclopropyl, cyclobutyl, cyclopentyl, cyclohexyl, cycloheptyl and cyclooctyl, which, however, can also be substituted by, for example, $(C_1-C_4)$-alkyl. Examples of substituted cycloalkyl radicals are 4-methylcyclohexyl and 2,3-dimethylcyclopentyl.

$(C_6-C_{14})$-Aryl groups are, for example, phenyl, naphthyl, biphenylyl or fluorenyl, phenyl and naphthyl being preferred. The same applies to radicals such as aralkyl or arylcarbonyl. Aralkyl radicals are in particular benzyl and also 1- and 2-naphthylmethyl, which can also be substituted. Substituted aralkyl radicals are, for example, halobenzyl or $(C_1-C_4)$-alkoxybenzyl.

If phenyl is disubstituted, the substituents can be present in the 1,2-, 1,3- or 1,4-position to one another. The 1,3- and the 1,4-positions are preferred.

Heterocycles within the meaning of the above definitions are, for example, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindazolyl, indazolyl, phthalazinyl, quinolyl, isoquinolyl, quinoxalinyl, quinazolinyl, cinnolinyl or a benzo-fused, cyclopenta-, cyclohexa- or cyclohepta-fused derivative of these radicals.

These heterocycles can be substituted on a nitrogen atom by oxides, $(C_1-C_7)$-alkyl, for example methyl or ethyl, phenyl or phenyl-$(C_1-C_4)$-alkyl, for example benzyl, and/or on one or more carbon atoms by $(C_1-C_4)$-alkyl, halogen, hydroxyl, $(C_1-C_4)$-alkoxy, for example methoxy, phenyl-$(C_1-C_4)$-alkoxy, for example benzyloxy, or oxo and can be partially or completely saturated.

Radicals of this type are, for example, 2- or 3-pyrrolyl, phenylpyrrolyl, for example 4- or 5-phenyl-2-pyrrolyl, 2-furyl, 2-thienyl, 4-imidazolyl, methylimidazolyl, for example 1-methyl-2-, 4- or 5-imidazolyl, 1,3-thiazol-2-yl, 2-, 3- or 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy, 5-benzyloxy, 5-chlorine or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl. Partially hydrogenated or completely hydrogenated heterocyclic rings are, for example, dihydropyridinyl, pyrrolidinyl, for example 2-, 3- or 4-N-methylpyrrolidinyl, piperazinyl, morpholinyl, thiomorpholinyl, tetrahydrothienyl, benzodioxolanyl.

Halogen represents fluorine, chlorine, bromine or iodine, in particular fluorine or chlorine.

Natural and unnatural amino acids can be present, if they are chiral, in the D- or L-form. α-Amino acids are preferred. For example, the following may be mentioned (cf. Houben-Weyl, Methoden der organischen Chemie (Methods of organic chemistry), Volume XV/1 and 2, Stuttgart, 1974):

Aad, Abu γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Set, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid and 2-(p-chlorophenyl)aminoacetic acid.

Amino acid side chains are understood as meaning side chains of natural or unnatural amino acids. Azaamino acids are natural or unnatural amino acids, the central component —CHR— or —CH$_2$— being replaced by —NR— or —NH— respectively.

Suitable radicals of an imino acid are in particular radicals of heterocycles from the following group:

Pyrrolidine-2-carboxylic acid; piperidine-2-carboxylic acid; tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-aza-bicyclo-[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]-heptane)-2,3-pyrrolidine-5-carboxylic acid; spiro-(bicyclo[2.2.2]octane)-2,3-pyrrolidine-5-carboxylic acid; 2-azatricyclo[4.3.0.1$^{6,9}$]-decane-3-carboxylic acid; decahydrocyclohepta[b]pyrrole-2-carboxylic acid; decahydrocyclooocta[c]pyrrole-2-carboxylic acid; octahydro-cyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid; hydroxyproline-2-carboxylic acid; which can all be optionally substituted (see the following formulae):

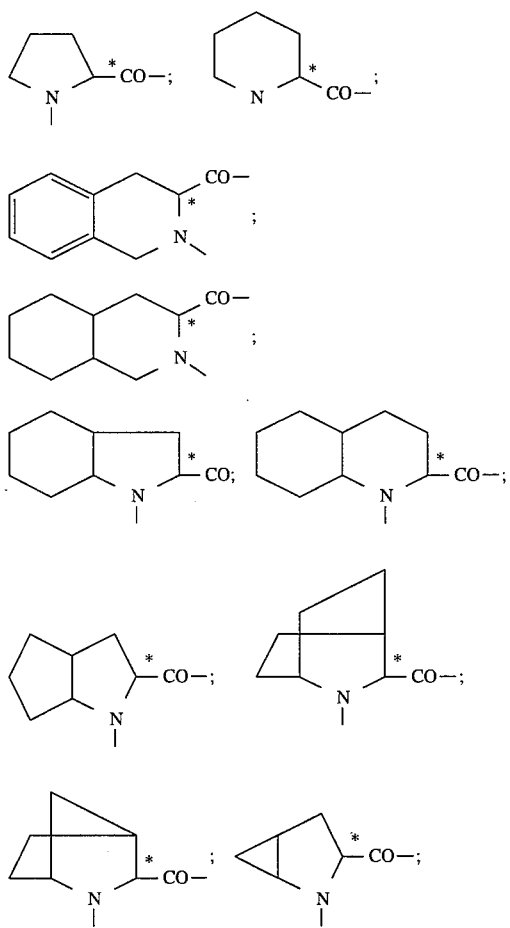

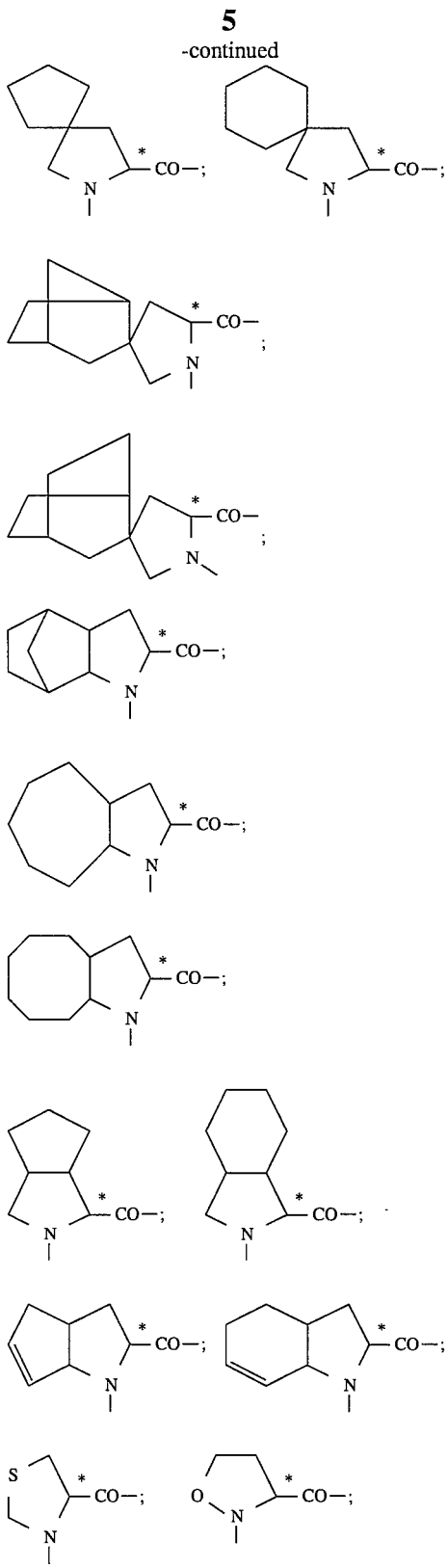

The heterocycles on which the abovementioned radicals are based are known, for example, from U.S. Pat. Nos. 4,344,949; 4,374,847; 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Dipeptides can contain natural or unnatural amino acids, imino acids and also azaamino acids as components. The natural or unnatural amino acids, imino acids, azaamino acids and dipeptides can furthermore also be present as esters or amides, such as, for example, methyl ester, ethyl amide, semicarbazide or ω-amino-$(C_4-C_8)$-alkyl amide.

Functional groups of the amino acids, imino acids and dipeptides can be present in protected form. Suitable protective groups such as, for example, urethane protective groups, carboxyl protective groups and side chain protective groups are described in Hubbuch, Kontakte (Merck) 1979, No. 3, pages 14 to 23 and in Büllesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboc, Acm, tert-butyl, OBzl, ONbzl, OMbzl, Bzl, Mob, Pic, Trt.

Physiologically tolerable salts of the compounds of the general formula I are in particular pharmaceutically utilisable or non-toxic salts.

Such salts are formed, for example, from compounds of the general formula I which contain acidic groups, for example carboxyl, using alkali metals or alkaline earth metals, such as, for example, Na, K, Mg and Ca, and also with physiologically tolerable organic amines, such as, for example, triethylamine and tris(2-hydroxyethyl)amine.

Compounds of the general formula I which contain basic groups, for example an amino group or a guanidino group, form salts with organic acids, such as, for example, hydrochloric acid, sulphuric acid or phosphoric acid and with organic carboxylic or sulphonic acids, such as, for example, acetic acid, citric acid, benzoic acid, maleic acid, fumaric acid, tartaric acid and p-toluenesulphonic acid.

The compounds of the general formula I according to the invention can contain optically active carbon atoms and can thus be present in the form of pure enantiomers or in the form of enantiomer mixtures. The present invention relates both to pure enantiomers and to enantiomer mixtures.

The compounds of the general formula I according to the invention can moreover contain mobile hydrogen atoms, i.e. can be present in various tautomeric forms. The present invention also relates to these tautomers.

Preferred compounds of the general formula I are those in which

Y denotes —$(CH_2)_m$—CO—, where m represents 1 or 2, or

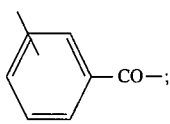

r denotes 1;

Z denotes oxygen or sulphur;

W denotes $(C_1-C_4)$-alkoxy, in particular methoxy, ethoxy or 2-propoxy;

R denotes hydrogen;

$R^1$ denotes $-(CH_2)_n-NH-X$, where n represents an integer from 1 to 4, $-CH_2-C_6H_4-(CH_2)_q-NH-X$ or $-CH_2-C_6H_4-(CH_2)_q-C-(=NX^2)-NH_2$, where q represents 0 or 1, but also where instead of

 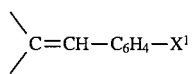

can be present;

X denotes hydrogen, $(C_1-C_6)$-alkoxycarbonyl, $(C_1-C_6)$-alkylcarbonyl, $(C_6-C_{14})$-aryl-$(C_1-C_6)$-alkoxycarbonyl or a radical of the formula II

in which R' and R" independently of one another represent hydrogen, $(C_1-C_6)$-alkoxycarbonyl or $(C_6-C_{14})$-aryl-$(C_1-C_6)$-alkoxycarbonyl;

$X^1$ denotes $-(CH_2)_q-NH-X$ or $-C(=NX^2)-NH_2$, where q represents 0 or 1;

$X^2$ denotes hydrogen, $(C_1-C_6)$-alkoxycarbonyl, $(C_1-C_6)$-alkylcarbonyl, $(C_6-C_{14})$-aryl-$(C_1-C_6)$-alkoxycarbonyl;

$R^2$ denotes hydrogen or methyl;

$R^3$ denotes hydrogen; and $R^4$ denotes $-CO-NH-R^5$, where $-NH-R^5$ represents an α-amino acid residue, its ω-amino-$(C_2-C_8)$-alkyl amide or its $(C_1-C_8)$-alkyl or benzyl ester.

α-Amino acid radicals representing $-NH-R^5$ are particularly preferably the valine, lysine, phenylalanine or phenylglycine or 4-chlorophenylglycine residue.

The compounds of the general formula I according to the invention can be prepared by fragment condensation of a compound of the general formula III

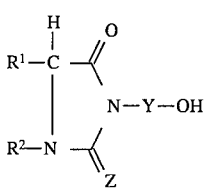

with a compound of the general formula IV

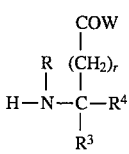

where the radicals R, $R^1$ to $R^4$ and r, Y, Z and W are defined as indicated above.

For condensation of the compounds of the general formula III with those of the general formula IV, the methods of peptide chemistry known per se are advantageously used (see, for example, Houben-Weyl, Methoden der organischen Chemie (Methods of organic chemistry), Volume 15/1 and 15/2, Stuttgart, 1974).

To do this, it is necessary as a rule that amino groups contained in $R^1$ and $R^4$ and W are protected by reversible protective groups. The same applies to the carboxyl groups of the compound of the general formula IV, which is preferably present as a benzyl or tert-butyl ester. Protection of amino groups is unnecessary if the amino groups to be generated are present as nitro or cyano groups and are only formed after coupling by hydrogenation.

After coupling, the protective groups present are removed in a suitable manner. For example, $NO_2$ groups (guanidino protection), benzyloxycarbonyl groups and benzyl esters can be removed by hydrogenation. Protective groups of the tert-butyl type are cleaved by acid, while the 9-fluorenylmethoxycarbonyl radical is removed by secondary amines.

The starting compounds of the general formula III can be obtained as follows:

By reaction of amino acids, N-alkylamino acids or preferably their methyl, ethyl, benzyl or tert-butyl esters, for example a compound of the general formula V

with an isocyanatoalkanecarboxylic acid ester, an isothiocyanatoalkanecarboxylic acid ester or an isocyanate or isothiocyanate of the aminobenzoic acid, for example of the general formula VI

in which $R^1$, $R^2$, Y, Z and m are defined as indicated above, urea derivatives are obtained, for example of the general formula VII

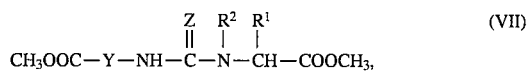

which cyclise by heating with acid with hydrolysis of the ester functions to give compounds of the general formula III

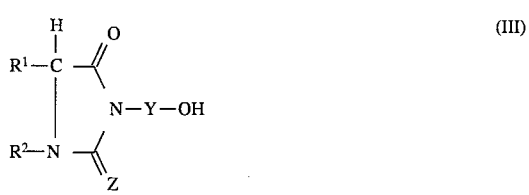

During the cyclisation, guanidino groups can be blocked by protective groups, such as $NO_2$ or Mtr. Amino groups in the side chain must likewise be present in protected form (for example as Boc or Z derivatives) or additionally as an $NO_2$ or cyano function which can later be reduced to the amino group or, in the case of the cyano group, also be converted into the formamidino group.

A further method for the preparation of compounds of the general formula III is the reaction of compounds of the general formula XI

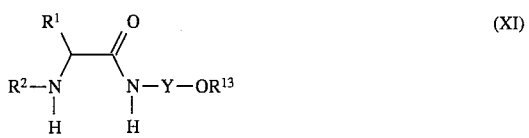

in which $R^1$, $R^2$ and Y are defined as indicated above and $R^{13}$ denotes, for example, $(C_1-C_6)$-alkyl, with phosgene, thiophosgene or corresponding equivalents and subsequent hydrolysis to the corresponding carboxylic acids (analogously to S. Goldschmidt and M. Wick, Liebigs Ann. Chem. 575 (1952) 217–231, C. Trapp, Chem. Ber. 61, (1928) 1431–1439).

Compounds of the general formula IIIb

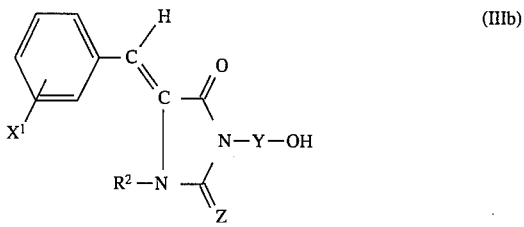

can be obtained by reaction of compounds of the general formula VIII

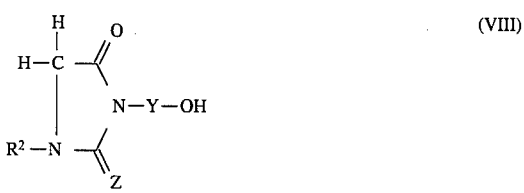

with aldehydes of the general formula IX

analogously to Gränacher and Landolt, Helv. Chim. Acta 10 (1927) 808.

Otherwise, hydantoins of the general formula Xa

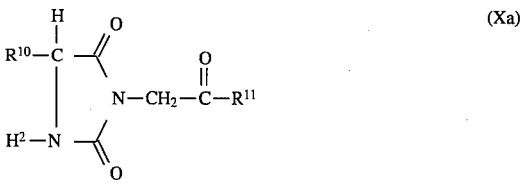

in which $R^{10}$ denotes any desired amino acid side chain and $R^{11}$ denotes an amide, an amino acid residue or a peptide residue, very commonly result by basic treatment of alkoxycarbonyl peptides or aralkoxycarbonyl peptides of the general formula X $$R^{12}-O-CO-NH-CHR^{10}-CO-NH-CH_2-CO-R^{11} \quad (X)$$

in which $R^{10}$ and $R^{11}$ are defined as indicated above and $R^{12}$ denotes benzyl or tert-butyl (J. S. Fruton and M. Bergmann, J. Biol. Chem. 145 (1942) 253–265; C. A. Dekker, S. P. Taylor, jr. and J. S. Fruton, J. Biol. Chem. 180 (1949) 155–173; M. E. Cox, H. G. Carg, J. Hollowood, J. M. Hugo, P. M. Scopes and G. T. Young, J. Chem. Soc. (1965) 6806–6813; W. Voelter and A. Altenburg, Liebigs Ann. Chem. (1983) 1641–1655; B. Schwenzer, E. Weber and G. Losse, J. Prakt. Chem. 327 (1985) 479–486). In this case, however, the N-terminal amino acid racemises and the hydantoin hydrolyses to the urea derivative $$HOCO-CHR^{10}-NH-CO-NH-CH_2-CO-R^{11}$$

(W. Voelter and A. Altenburg, Liebigs Ann. Chem. (1983) 1641–1655).

In comparison, a mild method is cyclisation to give the hydantoins from compounds of the general formula X by treatment with tetrabutylammonium fluoride in tetrahydrofuran under reflux (J. Pless, J. Org. Chem. 39 (1974) 2644–2646).

A further possibility of a mild cyclisation is trimethylsilylation of the peptide bond between the N-terminal amino acid and the following glycine using bistrimethylsilyltrifluoroacetamide in acetonitrile (4 hours under reflux) (J. S. Davies, R. K. Merritt and R. C. Treadgold, J. Chem. Soc. Perkin Trans. I (1982) 2939–2947).

The guanylation of the amino function can be carried out using the following reagents:

1. O-Methylisothiourea (S. Weiss and H. Krommer, Chemiker Zeitung 98 (1974) 617–618),
2. S-Methylisothiourea (R. F. Borne, M. L. Forrester and I. W. Waters, J. Med. Chem. 20 (1977) 771–776),
3. Nitro-S-methylisothiourea (L. S. Hafner and R. E. Evans, J. Org. Chem. 24 (1959) 1157),
4. Formamidinosulphonic acid (K. Kim, Y. -T. Lin and H. S. Mosher, Tetrah. Lett. 29 (1988) 3183–3186),
5. 3,5-Dimethyl-1-pyrazolylformamidinium nitrate (F. L. Scott, D. G. O'Donovan and J. Reilly, J. Amer. Chem. Soc. 75 (1953) 4053–4054).
6. N,N'-Di-tert-butoxycarbonyl-S-methylisothiourea (R. J. Bergeron and J. S. McManis, J. Org. Chem. 52 (1987) 1700–1703).
7. N-Alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A. Widding, P. Andrews, H. -P. Schulz and H. Thomas, Arzneim. Forsch./ Drug Res. 34 (1984) 531–542).

Formamidines can be prepared from the corresponding cyano compounds by addition of alcohols (for example methanol or ethanol) in acidic anhydrous medium (for example dioxane, methanol or ethanol) and subsequent treatment with ammonia in alcohols (for example isopropanol, methanol or ethanol) (G. Wagner, P. Richter and Ch. Garbe, Pharmazie 29 (1974) 12–55). A further method of preparing formamidines is the addition of $H_2S$ to the cyano group, followed by a methylation of the resulting thioamide and subsequent reaction with ammonia (GDR Patent No. 235,866).

The starting peptides of the general formula IV are as a rule synthesised stepwise from the C-terminal end. Formation of peptide bonds can be carried out using the known coupling methods of peptide chemistry.

The compounds of the general formula I and their physiologically tolerable salts can be administered as medicines per se on their own, in mixtures with one another or in the form of pharmaceutical preparations which permit enteral or parenteral use and which contain, as active constituent, an effective dose of at least one compound of the general formula I or of a salt thereof, in addition to customary pharmaceutically innocuous excipients and additives. The preparations normally contain about 0.5 to 90% by weight of the therapeutically active compound.

The medicines can be administered orally, for example in the form of pills, tablets, coated tablets, sugar-coated tablets, granules, hard and soft gelatine capsules, solutions, syrups, emulsions, suspensions or aerosol mixtures. Administration can also be carried out, however, rectally, for example in the form of suppositories, or parenterally, for example in the form of injection solutions or microcapsules, percutaneously, for example in the form of ointments or tinctures or nasally, for example in the form of nasal sprays.

The pharmaceutical preparations can be prepared in a manner known per se, pharmaceutically inert inorganic or organic excipients being used. For the preparation of pills, tablets, coated tablets and hard gelatine capsules, lactose, maize starch or derivatives thereof, talc, stearic acid or its salts, etc., for example, can be used. Excipients for soft gelatine capsules and suppositories are, for example, fats, waxes, semi-solid and liquid polyols, natural or hardened oils, etc. Suitable excipients for the preparation of solutions and syrups are, for example, water, sucrose, invert sugar, glucose, polyols etc. Suitable excipients for the preparation of injection solutions are water, alcohols, glycerol, polyols or vegetable oils, etc. Suitable excipients for microcapsules or implants are, for example, copolymers of glycolic acid and lactic acid.

Apart from the active compounds and excipients, the pharmaceutical preparations can additionally contain additives such as, for example, fillers, extenders, disintegrants, binders, lubricants, wetting agents, stabilisers, emulsifiers, preservatives, sweeteners, colorants, flavourings or aromatisers, thickeners, diluents, buffer substances, and also solvents or solubilisers or agents for achieving a depot effect as well as salts for changing the osmotic pressure, coating agents or antioxidants. They can also contain two or more compounds of the general formula I or their physiologically tolerable salts and additionally one or more other therapeutically active substances.

Other therapeutically active substances of this type are, for example, agents promoting the circulation, such as dihydroergocristine, nicergoline, buphenine, nicotinic acid and its esters, pyridylcarbinol, bencyclan, cinnarizine, naftidrofuryl, raubasine and vincamine; positively inotropic compounds, such as digoxin, acetyldigoxin, metildigoxin and lanthanoglycosides; coronary dilators, such as carbochromen; dipyramidol, nifedipine and perhexiline; antianginal compounds, such as isosorbide dinitrate, isosorbide mononitrate, glycerol nitrate, molsidomine and verapamil; β-blockers, such as propranolol, oxprenolol, atenolol, metoprolol and penbutolol. The compounds may moreover be combined with other nootropio substances, such as, for example, piracetam, or CNS-active substances, such as pirlindol, sulpiride, etc.

The dose can vary within wide limits and is to be adapted to the individual conditions in each individual case. In general, in the case of oral administration a daily dose of about 0.1 to 1 mg/kg, preferably 0.3 to 0.5 mg/kg, of body weight is appropriate to achieve effective results, in the case of intravenous administration the daily dose is in general about 0.01 to 0.3 mg/kg, preferably 0.05 to 0.1 mg/kg, of body weight. The daily dose is normally divided, in particular in the case of the administration of relatively large amounts, into several, for example 2, 3 or 4, part administrations. In some cases, depending on individual behaviour, it may be necessary to deviate upwards or downwards from the given daily dose. Pharmaceutical preparations normally contain 0.2 to 50 mg, preferably 0.5 to 10 mg, of active compound of the general formula I or one of its physiologically tolerable salts per dose.

The compounds of the formula I according to the invention have the ability to inhibit cell-cell adhesion which is due to the interaction of Arg-Gly-Asp-containing proteins, such as fibronectin, fibrinogen or the yon Willebrand factor, with the so-called integrins. Integrins are transmembrane glycoproteins, receptors for Arg-Gly-Asp-containing cell matrix glycoproteins (E. Ruoslahti and M. D. Pierschbacher, Science 238 (1987) 491–497; D. R. Phillips, I. F. Charo, L. V. Parise and L. A. Fitzgerald, Blood 71 (1988) 831–843). They additionally inhibit the binding of other adhesive proteins, such as vitronectin, collagen and laminin, to the corresponding receptors on the surface of various types of cell.

The compounds of the general formula I according to the invention inhibit platelet aggregation and osteoclast binding to the bone surfaces.

The hydantoin derivatives of the general formula I are used acutely in risk of thrombosis and chronically in the prevention of arteriosclerosis and thrombosis, for example in the therapy and prophylaxis of arterial vascular diseases, such as in acute myocardial infarct, secondary prevention of myocardial infarct, reocclusion prophylaxis after lysis and dilatation (PCTA), unstable angina pectoris, transitory ischaemic attacks, strokes, coronary bypass operation including bypass reocclusion prophylaxis, pulmonaryl embolism, peripheral arterial occlusive disease, dissecting aneurysm; in the therapy of venous and microcirculatory vascular disorders, such as deep vein thrombosis, disseminated intravascular clotting, post-operative and postpartum trauma, surgical or infectious shock, septicaemia or in hyperactive platelet diseases, thrombotic thrombocytopenic purpura, preeclampsia, premenstrual syndrome, dialysis or extracorporeal circulation. Osteoporosis can also be prevented by inhibition of osteoclast binding to the bone surface.

The compounds are tested in particular for their inhibitory action in blood platelet aggregation and the adhesion of fibrinogen to blood platelets. Gel-filtered blood platelets from human donor blood are used, which are activated with ADP or thrombin.

EXAMPLES

The products were identified by mass spectra and/or NMR spectra.

Example 1

3-(5-(S)-(3-Methoxycarbonylaminopropyl)-2,4-dioxoimidazolidin-3-yl)-benzoyl-L-aspartyl(OMe)-L-phenylglycine methyl ester

Example 1a

N-(S)-(Benzyloxycarbonyl-(3-benzyloxycarbonylaminopropyl)-methyl)-N'-(3-ethoxycarbonylphenyl) urea 1.2 g (10.5 mmol) of N-ethylmorpholine are added dropwise at room temperature to 4.1 g (10.5 mmol) of Z-L-ornithine benzyl ester hydrochloride and 2 g (10.5 mmol) of ethyl 3-isocyanatobenzoate in 20 ml of dimethylformamide. The mixture is stirred at room temperature for 12 h and at 50° C. for 1 h, treated with potassium hydrogen sulphate solution and extracted with ethyl acetate, and the organic phase is dried and concentrated.

Yield: 4.1 g (71%)

Example 1b 3-(5-(S)-(3-Aminopropyl)-2,4-dioxoimidazolidin-3-yl)-benzoic acid hydrochloride 4.1 g (7.5 mmol) of N-(S)-(benzyloxycarbonyl-(3-benzyloxycarbonylaminopropyl)-methyl)-N'-(3-ethoxycarbonylphenyl) urea are heated under reflux for 1 h with 60 ml of 6 N hydrochloric acid. The mixture is then concentrated, and the residue is stirred with ethyl acetate and filtered off with suction.

Yield: 2.1 g (89%) Melting point: 193°–196° C.

Example 1c 3-(5-(S)-(3-Methoxycarbonylaminopropyl)-2,4-dioxoimidazolidin-3-yl)-benzoic acid 314 mg (1 mmol) of 3-(5-(S)-(3-aminopropyl)-2,4-dioxoimidazolidin-3-yl)-benzoic acid hydrochloride are dissolved in 5 ml of methanol and 5 ml of water. After addition of 130 mg (1.38 mmol) of methyl chloroformate, the mixture is adjusted to pH 7 at 10° C. with 0.1 N sodium hydroxide solution. The mixture is allowed to warm to room temperature, and is stirred for 4 h, acidified to pH 3 with potassium hydrogen sulphate solution and concentrated. The residue is stirred with water, filtered off with suction and dried.

Yield: 187 mg Melting point 192°–194° C.

Example 1d 3-(5-(S)-(Methoxycarbonylaminopropyl)-2,4-dioxoimidazolidin-3-yl)-benzoyl-L-aspartyl(OMe)-L-phenylglycine methyl ester 35 μl (0.28 mmol) of N-ethylmorpholine and 58 mg (0.28 mmol) of DCC are added at 0° C. to 87.5 mg (0.26 mmol) of 3-(5 -(S)-methoxycarbonylaminopropyl)-2,4-dioxoimidazolidin-3-yl)benzoic acid, 106.2 g (0.26 mmol) of H-Asp(OMe)-Phg-OMe trifluoroacetate and 35.1 mg (0.26 mmol) of hydroxybenzotriazole in 10 ml of dimethylformamide. The mixture is stirred at 0° C. for 1 h and at room temperature for 20 h, precipitated urea is filtered off and the filtrate is concentrated. The residue is taken up in ethyl acetate and washed with sodium hydrogen carbonate solution and potassium hydrogen sulphate solution, and the organic phase is dried and concentrated. The product is chromatographed for purification on silica gel.

Yield: 130 mg FAB-MS: 611 (M + H)$^+$

Example 2

3-(5-(S)-(Aminopropyl)-2,4-dioxoimidazolidin-3-yl)-benzoyl-L-aspartyl(OMe)-L-phenylglycine methyl ester Example 2a 3-(5-(S)-(3-t-Butoxycarbonylaminopropyl)-2,4-dioxoimidazolidin-3-yl)-benzoic acid 6.4 g (56 mmol) of N-ethylmorpholine are added dropwise at room temperature to 9 g (41 mmol) of di-tert-butyl pyrocarbonate and 9.1 g (29 mmol) of 3-(5-(S)-(3-aminopropyl)-2,4-dioxoimidazolidin-3-yl)-benzoic acid hydrochloride in 40 ml of dimethylformamide. The mixture is stirred at room temperature for 15 h, salt is filtered off, the filtrate is concentrated, the residue is treated with potassium hydrogen sulphate solution and the mixture is extracted with ethyl acetate. The organic phase is stirred with tert-butyl methyl ester and the product is filtered off with suction.

Yield: 5.9 g Melting point 174°–177620 C.

Example 2b 3-(5-(S)-(3-t-Butoxycarbonylaminopropyl)-2,4-dioxoimidazolidin-3-yl)-benzoyl-L-aspartyl(OMe)-L-phenylglycine methyl ester 0.1 ml (0.8 mmol) of N-ethylmorpholine and 180 mg (0.87 mmol) of DCC are added at 0° C. to 300 mg (0.8 mmol) of 3-(5-(S)-(3 -t-butoxycarbonylaminopropyl)-2,4-dioxoimidazolidin-3-yl)benzoic acid, 330 mg (0.8 mmol) of H-Asp(OMe)-Phg-OMe trifluoroacetate and 110 mg (0.8 mmol) of hydroxybenzotriazole in 15 ml of dimethylformamide. The mixture is stirred at 0° C. for 1 h and at room temperature for 20 h, precipitated urea is filtered off and the filtrate is concentrated. The residue is taken up in ethyl acetate and washed with sodium hydrogen carbonate solution and potassium hydrogen sulphate solution, and the organic phase is dried and concentrated. The product is chromatographed for purification on silica gel.

Yield: 490 mg

Example 2c 3-(5-(S)-(3-Aminopropyl)-2,4-dioxoimidazolidin-3-yl)benzoyl-L-aspartyl(OMe)-L-phenylglycine methyl ester 490 mg (0.75 mmol) of 3-(5-(S)-(3-t-butoxycarbonylaminopropyl)-2,4-dioxoimidazolidin-3 -yl)benzoyl-L-aspartyl(OMe)-L-phenylglycine methyl ester are treated with 0.7 mol of 90% strength trifluoroacetic acid and 10 ml of methylene chloride. The mixture is stirred at room temperature for 20 h and concentrated in a high vacuum, and the residue is chromatographed for purification on Sephadex LH20 using a homogeneous mixture of butanol/glacial acetic acid/water.

Yield: 370 mg (74%) Melting point: 40°–45° C.

The following compounds can be prepared analogously to Examples 1 and 2.

Example 3

3-(5-(S)-(3-Acetylaminopropyl)-2,4-dioxoimidazolidin-3-yl)benzoyl-L-aspartyl(OMe)-L-phenylglycine methyl ester 1.50 g (4.70 mmol) of 3-(5-(S)-(3-acetamidopropyl-2,4-dioxoimidazolin-3-yl)benzoic acid and 1.92 g (4.70 mmol) of L-aspartyl(OMe)-L-phenylglycine-OMe are dissolved in 70 ml of DMF and the mixture is treated at 0° C. with stirring with 1.07 g (5.17 mmol) of dicyclohexylcarbodiimide, 0.63 g (4.70 mmol) of hydroxybenzotriazole and 0.6 ml (4.70 mmol) of N-ethylmorpholine. After 24 h, the solid is filtered off and the filtrate is concentrated in vacuo. The residue is taken up in ethyl acetate, washed with saturated sodium hydrogen carbonate solution and water, dried and concentrated in a rotary evaporator. The residue is chromatographed on silica gel (dichloromethane/methanol 98:2 and 95:5). The fractions which contain substance are freeze-dried.

Yield: 0.65 g (23%) Melting point: 60°–75° C. $[\alpha]_D^{20}=$ +4.35° (c=0.92, methanol) FAB-MS: 592.2 [M+H]$^+$

Example 4

(5-(R,S)-(4-Formamidinobenzyl)-2,4-dioxoimidazolidin-3-yl)acetyl-L-aspartyl(OBz)-L-valine benzyl ester

Example 5

(5-(S)-(4-Aminobutyl)-2,4-dioxoimidazolidin-3-yl)acetyl-L-aspartyl(OEt)-L-lysine ethyl ester

Example 6

(5-(4-Isopropyloxycarbonylaminomethylbenzylidene)-2,4-dioxoimidazolidin-3-yl)acetyl-L-aspartyl(O-iPr)-L-valine methyl ester

Example 7

(5-(4-Methoxycarbonylformamidinobenzylidene)-2,4-dioxoimidazolidin-3-yl)acetyl-L-aspartyl-L-phenylglycine

Example 8

(5-(S)-(3-Dimethoxycarbonylguanidinopropyl)-4-oxo-2-thioxoimidazolidin-3-yl)acetyl-L-aspartyl(OMe)-L-phenylglycine isopropyl ester

Example 9

(5-(4-Ethoxycarbonylformamidinobenzylidene)-1-methyl-2,4-dioxoimidazolidin-3-yl)acetyl-L-aspartyl(OEt)-L-Phenylglycine ethyl ester

Example 10

(5-(R,S)-(4-Formamidinobenzyl)-2,4-dioxoimidazolidin-3-yl)acetyl-L-aspartyl(OMe)-L-phenylglycine methyl ester

Example 11

(5-(S)-(4-Methoxycarbonylaminobutyl)-2,4-dioxoimidazolidin-3-yl)-propionyl-L-glutamyl-L-valine

Example 12

(5-(4-Acetylformamidinobenzylidene)-2,4-dioxoimidazolidin-3-yl)-acetyl-L-aspartyl(OMe)-L-phenylglycine methyl ester

Example 13

(5-(4-Methoxycarbonylformamidinobenzylidene)-2,4-dioxoimidazolidin-3-yl)acetyl-L-aspartyl(OMe)-L-phenylglycine methyl ester

Example 14

(5-(4-Aminomethylbenzylidene)-2,4-dioxoimidazolidin-3-yl)acetyl-L-aspartyl(OtBu)-L-phenylglycine methyl ester

Example 15

(5-(S)-(4-Guanidinobenzyl)-2,4-dioxoimidazolidin-3-yl)acetyl-L-aspartyl(OMe)-L-phenylglycine methyl ester

Example 16 a) (5-(S,R)-(4-Formamidinobenzyl)-2,4-dioxoimidazolidin-3-yl)-acetyl-L-aspartyl(O-isopropyl)-L-phenylglycine tert-butyl ester acetate 880 mg of dicyclohexylcarbodiimide are added at 0° C. to a suspension of 1.6 g ( 4 mmol ) of H-L-aspartyl(O-isopropyl )-L-phenylglycine tert-butyl ester hydrochloride, 1.16 g of (5-(S,R)( 4-formamidinobenzyl)-2,4-dioxoimidazolidin-3-yl )acetic acid and 540 mg of HOBt in 25 ml of dimethylformamide. The mixture is stirred at 0° C. for 1 hour and at room temperature for 3 hours. The precipitate is then filtered off with suction and the filtrate is concentrated and the residue is chromatographed on silica-gel in a mixture of methylene chloride, methanol, water and acetic acid in the ratio 85:15:2:2. After concentration, the residue is freeze-dried.

Yield: 2.29 g $[\alpha]_D^{23}=-0.8°$ (c=1, methanol)

Example 17

(5-(S,R)-(4-Formamidinobenzyl)-2,4-dioxoimidazolidin-3-yl)acetyl-L-aspartyl (O-isopropyl)-L-phenylglycine 1.2 g of (5-(S,R)-(4-formamidinobenzyl)-2,4-dioxoimidazolidin-3-yl)acetyl-L-aspartyl(O-isopropyl)-L-phenylglycine tert-butyl ester acetate are dissolved in 12 ml of 90% strength aqueous trifluoroacetic acid. The mixture is allowed to stand at room temperature for one hour and concentrated. The residue cannot be partitioned between water and ether. The insoluble substance is filtered off with suction and washed with ether.

Yield: 560 mg $[\alpha]_D^{22}=-9.8°$ (c=1, methanol)

Example 18

(5-(S,R)-(4-Formamidinobenzyl)-2,4-dioxoimidazolidin-3-yl)acetyl-L-aspartyl (O-tert-butyl)-L-phenylglycine isopropyl ester acetate 2.29 g of dicyclohexylcarbodiimide are added to a suspension of 3.03 g of (5-(S,R)-(4-formamidinobenzyl)-2,4-dioxoimidazolidin-3-yl)acetic acid, 4.18 g of H-L-aspartyl(O-tert-butyl)-L-phenylglycine isopropyl ester hydrochloride and 1.4 g of HOBt in 25 ml of dimethylformamide. The mixture is stirred at 0° C. for 1 hour and at room temperature for 5 hours. The precipitate is then filtered off with suction and the filtrate is concentrated and the residue is chromatographed on silica gel in a mixture of methylene chloride, methanol, water and acetic acid in the ratio 85:15:2:2. After concentration, the residue is freeze-dried.

Yield: 4.9 g $[\alpha]_D^{22}=-0.4°$ (c=1, methanol)

EXAMPLE 19

(5-(S,R)-(4-Formamidinobenzyl)-2,4-dioxoimidazolidin-3-yl)acetyl-L-aspartyl-L-phenylglycine diisopropyl ester acetate 440 mg of dicyclohexylcarbodiimide are added at 0° C. to a suspension of 580.6 mg of (5-(S,R)-(4-formamidinobenzyl)-2,4-dioxoimidazolidin-3-yl)acetic acid, 773.8 mg of H-L-aspartyl-L-phenylglycine diisopropyl ester hydrochloride and 270 mg of HOBt in 25 ml of dimethylformamide. The mixture is stirred at 0° C. for 1 hour and at room temperature for 5 hours. The precipitate is then filtered off with suction and the filtrate is concentrated and the residue is chromatographed on silica gel in a mixture of methylene chloride, methanol, water and acetic acid in the ratio 85:15:2:2. After concentration, the residue is freeze-dried.

Yield: 1.04 g $[\alpha]_D^{24}=-4.0°$ (c=1, methanol)

EXAMPLE 20

3-(51(S)-(3-(1-Acetoxyethoxycarbonylamino)propyl)-
2,4-dioxoimidazolidin-3
-yl)benzoyl-L-aspartyl(OMe)-L-phenylglycine
methyl ester a)
3-(5-(S)-(3-(1-Acetoxyethoxycarbonylamino)propyl)-
2,4-dioxoimidazolidin-3-yl)benzoic acid 2.50 g (7.97 mmol) of 3-(5-(S)-3-aminopropyl-2,4-dioxoimidazolidin-3-yl)benzoic acid and 2.15 g (7.97 mmol) of 1-acetoxyethyl p-nitrophenyl carbonate are dissolved in 50 ml of DMF, treated with 3.33 ml (24 mmol) of triethylamine and stirred at room temperature for 3 d. The mixture is concentrated in vacuo and the residue is chromatographed on silica gel (dichloromethane/methanol/glacial acetic acid).

Yield: 1.95 g (60%) of oil b)
3-(5-(S)-(3-(1-Acetoxyethoxycarbonylamino)propyl)-
2,4-dioxoimidazolidin-3
-yl)benzoyl-L-aspartyl(OMe)-L-phenylglycine
methyl ester 0.42 g (1.03 mmol) of 3-(5-(S)-(3-(1-acetoxyethoxycarbonylamino)propyl)-2,4-dioxoimidazolidin- 3-yl)benzoic acid and 0.42 g (1.03 mmol) of L-aspartyl(OMe)-L-phenylglycine-OMe trifluoroacetate are dissolved in 15 ml of DMF and treated at 0° C. with stirring with 0.23 g (1.13 mmol) of dicyclohexylcarbodiimide, 0.14 g (1.03 mmol) of hydroxybenzotriazole and 0.13 ml (1.03 mmol) of N-ethylmorpholine. After 24 h, the solid is filtered off and the filtrate is concentrated in vacuo. The residue is taken up in ethyl acetate, and the solution is washed with saturated sodium hydrogen carbonate solution and water, dried and concentrated in a rotary evaporator. The residue is chromatographed on silica gel ( dichloromethane/methanol 95:5). The fractions which contain substance are concentrated in vacuo.

Yield: 0.22 g (32%) Melting point: 60°–66° C. $[\alpha]_D^{20}=$ +21.58° (c=0.695, methanol) FAB-MS: 684.2 ]M+H]$^+$

EXAMPLE 21

3-[5-(S)-(3-Benzyloxycarbonylaminopropyl)-4-oxo-
2-thioxoimidazolidin-3
-yl)benzoyl-L-aspartyl-L-phenylglycine

FAB-MS: 676.4 [M+H]$^+$

EXAMPLE 22

3-[5-(S)-(3-Acetylaminopropyl)-2,4-
dioxoimidazolidin-3-yl)-benzoyl-L-aspartyl-
L-phenylglycine

FAB-MS: 568.2 [M+H]$^+$

EXAMPLE 23

3-[5-(S)-(3-Acetylaminopropyl)-2,4-
dioxoimidazolidin-3-yl)-benzoyl-L-aspartyl-
L-phenylglycine diisopropyl ester

FAB-MS: 652.3 [M+H]$^+$

EXAMPLE 24

3-[5-(S)-(Guanidinomethyl)-2,4-
dioxoimidazolidin-3-yl)benzoyl-L-aspartyl-
L-phenylglycine diisopropyl ester

FAB-MS: 624.2 [M+H]$^+$

EXAMPLE 25

3-[5-(S)-(Methoxycarbonylguanidinomethyl)-2,4-
dioxoimidazolidin-3-yl)benzoyl-L-aspartyl-
L-phenylglycine diisopropyl ester

FAB-MS: 682.3 [M+H]$^+$

EXAMPLE A

Emulsions containing 3 mg of active compound per 5 ml can e prepared according to the following recipe:

| | |
|---|---|
| Active compound | 0.06 g |
| Neutral oil | q.s. |
| sodium carboxymethycellulose | 0.6 g |
| Polyoxyethylene stearate | q.s. |
| Pure glycerol | 0.6 to 2 g |
| Aromatics | q.s. |
| Water (demineralised or distilled) | to 100 ml |

EXAMPLE B

Tablets can be prepared according to the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

EXAMPLE C

The following composition is suitable for the preparation of soft gelatine capsules containing 5 mg of active compound per capsule:

| | |
|---|---|
| Active compound | 5 mg |
| Mixture of triglycerides from coconut oil | 150 mg |
| Capsule contents | 155 mg |

EXAMPLE D

The following formulation is suitable for the preparation of sugar-coated tablets:

| | |
|---|---|
| Active compound | 3 mg |
| Maize starch | 100 mg |
| Lactose | 55 mg |
| Sec. calcium phosphate | 30 mg |
| Soluble starch | 3 mg |
| Magnesium stearate | 5 mg |
| Colloidal silica | 4 mg |

EXAMPLE E

Sugar-coated tablets containing an active compound according to the invention and another therapeutically active substance:

| | |
|---|---|
| Active compound | 6 mg |
| Propanolol | 40 mg |
| Lactose | 90 mg |
| Maize starch | 90 mg |
| Sec. calcium phosphate | 34 mg |
| Soluble starch | 3 mg |
| Magnesium stearate | 3 mg |
| Colloidal silica | 4 mg |
| | 270 mg |

EXAMPLE F

Sugar-coated tablets containing an active compound according to the invention and another therapeutically active substance:

| | |
|---|---|
| Active compound | 5 mg |
| Pirlindol | 5 mg |
| Lactose | 60 mg |
| Maize starch | 90 mg |
| Sec. calcium phosphate | 30 mg |
| Soluble starch | 3 mg |
| Magnesium stearate | 3 mg |
| Colloidal silica | 4 mg |
| | 200 mg |

EXAMPLE G

Capsules containing an active compound according to the invention and another therapeutically active substance:

| | |
|---|---|
| Active compound | 5 mg |
| Nicergoline | 5 mg |
| Maize starch | 185 mg |
| | 195 mg |

EXAMPLE H

Injection solutions containing 1 mg of active compound per ml can be prepared according to the following recipe:

| | |
|---|---|
| Active compound | 1.0 mg |
| Polyethylene glycol 400 | 0.3 mg |
| Sodium chloride | 2.7 mg |
| Water for injection purposes to | 1 ml |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Compounds of the formula I

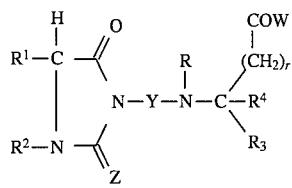

in which

Y denotes —$(CH_2)_m$—CO—, where m represents an integer from 1 to 4, or

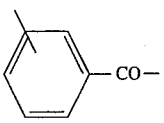

r denotes a number from 0 to 3;

Z denotes oxygen or sulphur;

W denotes $(C_1-C_{28})$-alkoxy, $(C_6-C_{14})$-aryl-$(C_1-C_6)$-alkoxy, $(C_6-C_{14})$-aryloxy, amino or mono- or di-$(C_1-C_{18})$-alkylamino;

R denotes hydrogen or $(C_1-C_6)$-alkyl;

$R^1$ denotes —$(CH_2)_n$—NH—X, where n represents an integer from 1 to 6, —$(CH_2)_p$—$C_6H_4$—NH—X or —$(CH_2)_p$—$C_6H_4$—$(CH_2)_q$—C(=$NX^2$)—$NH_2$, where p represents an integer from 1 to 3 and q represents a number from 0 to 2, but also where instead of

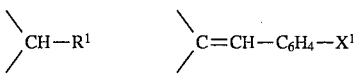

can be present;

X denotes hydrogen, $(C_1-C_6)$-alkyl, $(C_1-C_6)$-alkoxycarbonyl, $(C_1-C_6)$-alkylcarbonyl, $(C_1-C_{18})$-alkylcarbonyloxy-$(C_1-C_6)$-alkoxycarbonyl, $(C_6-C_{14})$-aryloxycarbonyl, $(C_6-C_{14})$-aryl-$(C_1-C_6)$-alkoxycarbonyl, cyano, hydroxyl, $(C_1-C_6)$-alkoxy, amino or a radical of the formula II

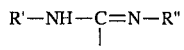

in which R' and R" independently of one another represent hydrogen, $(C_1-C_6)$-alkyl, $(C_1-C_6)$-alkoxycarbonyl, $(C_1-C_6)$-alkylcarbonyl, $(C_1-C_{18})$-alkylcarbonyloxy-$(C_1-C_6)$-alkoxycarbonyl, $(C_6-C_{14})$-aryloxycarbonyl, $(C_6-C_{14})$-aryl-$(C_1-C_6)$-alkoxycarbonyl, cyano, hydroxyl, $(C_1-C_6)$-alkoxy or amino;

$X^1$ denotes —$(CH_2)_q$—NH—X or —$(CH_2)_q$—C(=$NX^2$)—$NH_2$;

$X^2$ denotes hydrogen, $(C_1-C_6)$-alkyl, $(C_1-C_6)$-alkoxycarbonyl, $(C_1-C_6)$-alkylcarbonyl, $(C_1-C_{18})$-alkylcarbonyloxy-$(C_1-C_6)$-alkoxycarbonyl, $(C_6-C_{14})$-aryloxycarbonyl, $(C_6-C_{14})$-aryl-$(C_1-C_6)$-alkoxycarbonyl, cyano, hydroxyl, $(C_1-C_6)$-alkoxy or amino;

$R^2$ denotes hydrogen or $(C_1-C_6)$-alkyl;

$R^3$ denotes hydrogen or phenyl;

$R^4$ denotes hydrogen, —$COOR^5$, —CO—$N(CH_3)$—$R^5$ or —CO—NH—$R^5$;

$R^5$ denotes hydrogen, or $(C_1-C_{28})$-alkyl, which is optionally monosubstituted or polysubstituted by identical or different radicals from the series consisting of hydroxyl, hydroxycarbonyl, aminocarbonyl, mono- or di-($C_1$–$C_{18}$)-alkylaminocarbonyl, amino-($C_2$–$C_{14}$)-alkylaminocarbonyl, amino-($C_1$–$C_3$)-alkylphenyl-($C_1$–$C_3$)-alkylaminocarbonyl, ($C_1$–$C_{18}$)-alkylcarbonylamino-($C_1$–$C_3$)-alkylphenyl-($C_1$–$C_3$)-alkylaminocarbonyl, $C_1$–$C_{18}$)-alkylcarbonylamino-($C_2$–$C_{14}$)-alkylaminocarbonyl, phenyl-($C_1$–$C_8$)-alkoxycarbonyl, amino, mercapto, ($C_1$–$C_{18}$)-alkoxy, ($C_1$–$C_{18}$)-alkoxycarbonyl, ($C_3$–$C_8$)-cycloalkyl, halogen, nitro, trifluoromethyl or a radical $R^6$;

$R^6$ denotes ($C_6$–$C_{14}$)-aryl, ($C_6$–$C_{14}$)-aryl-($C_1$–$C_8$)-alkyl, a monocyclic or bicyclic 5- to 12-membered heterocyclic ring which can be aromatic, partially hydrogenated or completely hydrogenated and which, as the heteroelement, can contain one, two or three identical or different nitrogen, oxygen or sulphur atoms, or denotes a radical $R^7$, where the aryl radical and, independently thereof, the heterocyclic radical can be optionally mono-substituted or polysubstituted by identical or different radicals from the series consisting of ($C_1$–$C_{18}$)-alkyl, ($C_1$–$C_{18}$)-alkoxy, halogen, nitro and trifluoromethyl;

$R^7$ denotes —$NR^8R^9$, —$OR^8$, —$SR^8$, an amino acid side chain, a natural or unnatural amino acid residue, imino acid residue, optionally N-($C_1$–$C_6$)-alkylated or ($C_6$–$C_{14}$)-aryl-($C_1$–$C_6$)-alkylated azaamino acid residue or dipeptide residue, in which the peptide bond can be reduced to NH—$CH_2$, and also their esters and amides, where free functional groups can optionally be substituted by hydrogen or hydroxymethyl or protected by protective groups customary in peptide chemistry, or denotes a radical —$COR^{7'}$; in which $R^{7'}$ is defined as $R^7$;

$R^8$ denotes hydrogen, ($C_2$–$C_{18}$)-alkyl, ($C_8$–$C_{14}$)-aryl-($C_1$–$C_8$)-alkyl, ($C_1$–$C_{18}$)-alkylcarbonyl, ($C_1$–$C_{18}$)-alkoxycarbonyl, ($C_8$–$C_{14}$)-arylcarbonyl, ($C_8$–$C_{14}$)-aryl-($C_1$–$C_8$)-alkylcarbonyl, or ($C_6$–$C_{14}$)aryl-($C_1$–$C_{18}$)-alkoxycarbonyl, where the alkyl groups can optionally be substituted by an amino group, a natural or unnatural amino acid residue, imino acid residue, optionally N-($C_1$–$C_8$)alkylated or ($C_8$–$C_{14}$)-aryl-($C_1$–$C_8$)-alkylated azaamino acid residue or a dipeptide residue, in which the peptide bond can be reduced to NH—$CH_2$; and $R^9$ denotes hydrogen, ($C_1$–$C_{18}$)-alkyl, ($C_8$–$C_{14}$)-aryl or ($C_8$–$C_{14}$)-aryl-($C_1$–$C_8$)-alkyl;

and there physiologically tolerable salts, extending compounds of the formula I, wherein, simultaneously, r denotes 1;

Z denotes oxygen;

W denotes tert-butoxy;

R denotes hydrogen;

$R^1$ denotes —$(CH_2)_k$—NH—$X^a$ where k represents an integer from 3 to 5, —$CH_2$—$C_6H_4$—NH—$X^a$ or —$CH_2$—$C_6H_4$—C(=NH)—$NH_2$ or where instead of

 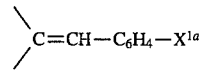

is present;

$X^a$ denotes hydrogen, ($C_1$–$C_6$)-alkyl or a radical of the formula

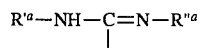

in which $R'^a$ and $R''^a$ independently of one another denote hydrogen or ($C_1$–$C_6$)-alkyl;

$X^{1a}$ has one of the meanings of $X^a$ or denotes —C(=NH)—$NH_2$.

2. Compounds according to claim 1, characterised in that in general formula I

Y denotes —$(CH_2)_m$—CO—, where m represents 1 or 2, or

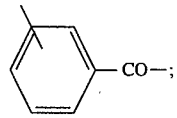

r denotes 1;

Z denotes oxygen or sulphur;

W denotes ($C_1$–$C_4$)-alkoxy, in particular methoxy, ethoxy or 2-propoxy;

R denotes hydrogen;

$R^1$ denotes —$(CH_2)_n$—NH—X, where n represents an integer from 1 to 4, —$CH_2$—$C_6H_4$—$(CH_2)_q$—NH—X or —$CH_2$—$C_6H_4$—$(CH_2)_q$—C—(=$NX^2$)—$NH_2$, where q represents 0 or 1, but also where instead of

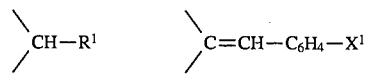

can be present;

X denotes hydrogen, ($C_1$–$C_6$)-alkoxycarbonyl, ($C_1$–$C_6$)-alkylcarbonyl, ($C_6$–$C_{14}$)-aryl-($C_1$–$C_6$)-alkoxycarbonyl or a radical of the formula II

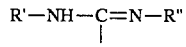 (II)

in which R' and R" independently of one another represent hydrogen, ($C_1$–$C_6$)-alkoxycarbonyl or ($C_6$–$C_{14}$)-aryl-($C_1$–$C_6$)-alkoxycarbonyl;

$X^1$ denotes —$(CH_2)_q$—NH—X or —C(=$NX^2$)—$NH_2$, where q represents 0 or 1;

$X^2$ denotes hydrogen, ($C_1$–$C_6$)-alkoxycarbonyl, ($C_1$–$C_6$)-alkylcarbonyl ($C_6$–$C_{14}$)-aryl-($C_1$–$C_6$)-alkoxycarbonyl;

$R^2$ denotes hydrogen or methyl;

$R^3$ denotes hydrogen; and $R^4$ denotes —CO—NH—$R^5$, where —NH—$R^5$ represents an α-amino acid residue, its ω-amino-($C_2$–$C_8$)-alkyl amide or its ($C_1$–$C_8$)-alkyl or benzyl ester.

3. Compounds according to claim 2, characterised in that α-amino acid radicals representing —NH—$R^5$ are the valine, lysine, phenylalanine, phenylglycine or the 4-chlorophenylglycine radical.

4. Compounds according to claim 2, characterised in that the ω-amino-($C_2$–$C_8$)-alkyl amide is the 4-aminobutyl amide.

5. Process for the preparation of compounds of claims 1 to 4, characterised in that a fragment condensation of a compound of the general formula III

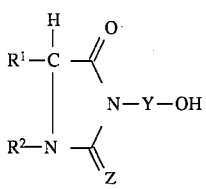

(III)

with the compound of the general formula IV

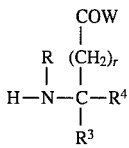

(IV)

where the radicals R, $R^1$ to $R^4$ and r, Y, Z and W are defined as indicated in claim 1, is carried out.

6. Process for inhibiting platelet aggregation, thromboses, and osteoclast binding to the bone surfaces comprising administering to a patient in need thereof an effective dose of a compound coming within the scope of formula I of claim 1.

7. Pharmaceutical preparation, characterized in that it contains one or more compounds coming within the scope of formula I of claim 1 or a physiologically tolerable salt thereof as active compound together with pharmaceutically acceptable excipients and additives.

8. Process for the production of a pharmaceutical preparation containing one or more compounds coming within the scope of formula I of claim 1 or a physiologically tolerable salt thereof, characterised in that these are brought into a suitable administration form together with pharmaceutically acceptable excipients and additives.

9. Compounds according to claim 1 in which Y denotes

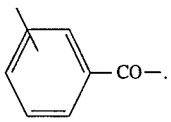

10. 3-(5-(S)-(3-(1-Acetoxyethoxycarbonylamino) propyl)-2,4-dioxoimidazolidin-3-yl)benzoyl-L-aspartyl(OMe)-L-phenylglycine methyl ester.

11. Process for inhibiting platelet aggregation, thromboses, and osteoclast binding to the bone surfaces comprising administering to a patient in need thereof an effective dose of the compound according to claim 10.

12. Pharmaceutical preparation, characterised in that it contains the compound of claim 10 or a physiologically tolerable salt thereof as active compound together with pharmaceutically acceptable excipients and additives.

13. 3-(5-(S)-(3-Aminopropyl)-2,4-dioxoimidazolidin-3-yl)-benzoyl-L-aspartyl(OMe)-L-phenyl methyl ester.

14. 3-(5-(S)-(3-Acetylaminopropyl)-2,4-dioxoimidazolidin-3-yl)benzoyl-L-aspartyl(OMe)-L-phenylglycine methyl ester.

15. (5-(S,R)-(4-Formamidinobenzyl)-2,4-dioxoimidazolidin-3-yl)acetyl-L-aspartyl(O-isopropyl)-L-phenylglycine tert-butyl ester acetate.

16. (5-(S,R)-4-Formamidinobenzyl)-2,4-dioxoimidazolidin-3-yl)acetyl-L-aspartyl(O-isopropyl)-L-phenylglycine.

17. (5-(S,R)-(4-Formamidinobenzyl)-2,4-dioxoimidazolidin-3-yl)acetyl-L-aspartyl-L-phenylglycine diisopropyl ester acetate.

18. A compound according to claim 1 in which W denotes $(C_6-C_{14})$-aryl-$(C_1-C_8)$-alkoxy, $(C_6-C_{14})$-aryloxy, amino, or mono or di-$(C_1-C_{18})$-alkylamino.

* * * * *